United States Patent [19]

Beaulieu et al.

[11] Patent Number: 5,550,291
[45] Date of Patent: Aug. 27, 1996

[54] PROCESS FOR KEY INTERMEDIATES FOR HIV PROTEASE INHIBITORS

[75] Inventors: Pierre L. Beaulieu, Rosemère; Yvan Guindon, Montréal; Dominik M. Wernic, Laval, all of Canada

[73] Assignee: Bio-Mega/Boehringer Ingelheim Research, Inc., Laval, Canada

[21] Appl. No.: 434,691

[22] Filed: May 4, 1995

[30] Foreign Application Priority Data

Dec. 6, 1994 [CA] Canada .................................. 2137406

[51] Int. Cl.[6] ...................... C07C 209/26; C07C 209/54; C07C 209/68; C07C 209/82
[52] U.S. Cl. .................. 564/357; 564/305; 564/355; 564/356; 564/366; 564/372; 564/431; 564/433; 564/434; 564/437; 564/439; 564/442; 564/443; 564/502; 562/433; 562/439; 562/456
[58] Field of Search .................... 564/305, 355, 564/356, 357, 366, 372, 431, 433, 434, 437, 439, 442, 443, 502; 562/433, 439, 456

[56] References Cited

FOREIGN PATENT DOCUMENTS 0560268  9/1993  European Pat. Off. .
9323388  5/1993  WIPO .

OTHER PUBLICATIONS

S. Thaisrovongs, Annual Reports in Medicinal Chemistry, 1994, 29, 133.

N. A. Roberts et al., "Rational Design of Peptide–Based HIV Proteinase Inhibitors", Science, 1990, 248, 358–361.

D. P. Getman et al., "Discovery of a Novel Class of Potent HIV–1 Protease Inhibitors Containing the (R)–(Hydroxyethyl)urea Isoster", J. Med. Chem., 1993, 36, 288–291.

B. E. Evans et al., "A Sterocontrolled Synthesis of Hydroxyethylene Dipeptide Isoteres Using Novel, Chiral Aminoalkyl epoxides and γ–(Aminoalkyl) γ–Lactones", J. Org. Chem., 1985, 50, 4615–4625.

M. T. Reetz and J. Binder, "Protective Group Tuning in the Stereoselective Conversion of α–Amino Aldehydes Into Aminoalkyl Eopxides", Tetrahedron Letters, 1989, 30, 5425–5428.

A. Albeck and R. Persky, "Stereocontrolled Synthesis of Erythro N–Protected α–Amino Epoxides and Peptidyl Eopxides", Tetrahedron, 1994, 50, 6333–6346.

J. Barluenga et al., "The First Direct Preparation of Chiral Functionalised Ketones And Their Synthetic Uses", J. Chem. Co., Chem. Commun., 1994, 969–970.

*Primary Examiner*—W. Robinson H. Clark
*Attorney, Agent, or Firm*—Robert P. Raymond; Alan R. Stempel; Mary-Ellen M. Devlin

[57] ABSTRACT

Disclosed herein is a stereospecific synthesis amenable to the large scale preparation of a hydrochloric acid addition salt of a chlorohydrin of the formula

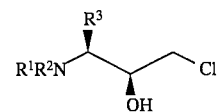

wherein $R^1$ and $R^2$ are amino protective groups and $R^3$ is an amino acid side chain or a protected amino acid side chain. The synthesis involves reacting an aldehyde of the formula

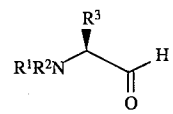

wherein $R^1$, $R^2$ and $R^3$ are as defined hereinbefore with (chloromethyl)lithium at −20° C. or below and contacting the resulting diastereoisomeric mixture of lithium alcoholates with aqueous hydrochloric acid to obtain a separable mixture of the hydrochloric acid addition salts of the chlorohydrin and its corresponding hydroxy diastereoisomer. The hydrochloric acid addition salt of the chlorohydrin is transformed readily into corresponding optionally aminoprotected aminoepoxides; for example, 3(S)-(tert-butyloxycarbonylamino)-1,2(S)-epoxy-4-phenyl-butane.

10 Claims, No Drawings

1

PROCESS FOR KEY INTERMEDIATES FOR HIV PROTEASE INHIBITORS

FIELD OF THE INVENTION

This invention relates to HIV protease inhibitors. More specifically, this invention relates to a process for the stereospecific synthesis of key intermediates for preparing hydroxyethylamine isosteres.

BACKGROUND OF THE INVENTION

HIV protease is an essential enzyme for the replication of human immunodeficiency virus (HIV), the causative agent of acquired immunodeficiency syndrome (AIDS). Within the last decade, the enzyme has become recognized as a virus-specific therapeutic target. As a result, much attention has been focused on the development of HIV protease inhibitors for the treatment of AIDS. For a recent review on the state of HIV protease inhibitors, see S. Thaisrivongs, Annual Reports In Medicinal Chemistry, 1994, 29, 133.

As noted in the latter review, potent HIV protease inhibitors have been realized by the placement of a hydroxyethylamine isostere (also known as a hydroxyethylamine transition state analog) in a peptide having the p17/p24 substrate cleavage site sequence.

Noteworthy reports describing HIV protease inhibitors with hydroxyethyamine isosteres incorporated therein include N. A. Roberts et al., Science, 1990, 248, 358; D. P. Getman et al., J. Med. Chem., 1993, 36, 288; and P. C. Anderson et al., European patent application, publication no. 560 268, Sep. 15, 1993.

As exemplified in the last three references, an often-used intermediate for the elaboration of the hydroxyethylamine isostere-containing inhibitors is an aminoepoxide intermediate represented by the following general formula A:

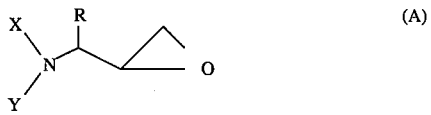

wherein X is an N-protective group, Y is hydrogen or an N-protective group, and R is a typical amino acid side chain; for example, phenylmethyl derived from phenylalanine, or protected amino acid side chain, for example, {4-(phenylmethoxy)phenyl}methyl derived from tyrosine.

Note that the above general formula for the aminoepoxide intermediate contains two asymmetric carbon atoms.

Preferred enantiomerically pure amino epoxide intermediates for the preparation of the hydroxyethylamine isostere containing HIV protease inhibitors are those in which the carbon atom bearing the nitrogen atom and the carbon atom bearing the oxygen atom both have the (S) configuration.

Hence, in view of high profile of the intermediates, a process for the preparation of the enantiomerically pure (S,S)-aminoepoxide intermediates, which meets the criteria of being efficient, safe and amenable to scale-up, is most desirable.

Paradoxically, the reported preparations of the desired enantiomerically pure aminoepoxide intermediates, or chemical equivalents thereof, do not meet the aforementioned three criterea.

More explicitly, B. E. Evans et al., J. Org. Chem., 1985, 50, 4615 reports the synthesis of enantiomerically pure aminoepoxide intermediates by reacting the corresponding Boc-α-amino aldehydes with dimethylsulfonium methylide and separating the resulting mixture of diastereoisomeric epoxides. This method suffers from the lack of stereoselectivity, the use of a hazardous combination of sodium hydride and dimethylsulfoxide, as well as the use of chromatography to separate diastereoisomers, a step not easily amenable to scale-up.

M. T. Reetz and J. Binder, Tetrahedron Letters, 1989, 30, 5425 describe a similar process involving the reaction of N,N-(doubly protected)-α-aminoaldehydes with dimethylsulfonium methylide. Although the N,N-(doubly protected)-α-aminoaldehyde lends itself to a more stereoselective conversion, the process suffers from the aforementioned disadvantages of safety and the need to separate the mixture of diastereoisomeric products by chromatography. The authors note on page 5428 (reference 8) that the separation of the diastereoisomeric products (aminoepoxide) is difficult and suggest the separation of later oxirane-ring opened products as a more practical method to diastereomerically pure products.

Recently, A. Albeck and R. Persky, Tetrahedron, 1994, 50, 6333 described a multistep process for preparing aminoepoxide intermediates. The process utilizes an α-(chloromethyl)-γ-N-(benzyloxycarbonyl) aminoketone precursor which is synthesized in turn by a step involving diazomethane. The use of diazomethane, a hazardous reagent, limits this process to small scale preparations.

Again recently, J. S. Ng et al., PCT patent application WO 93/23388, published Nov. 25, 1993 reported a process for preparing the aminoepoxide intermediate by reacting N,N-doubly protected-γ-amino aldehydes with a halomethyllithium reagent generated in situ from chloroiodomethane and butyllithium to give the aminoepoxide intermediate as a mixture of diastereoisomers. Although the isolation of two diastereomerically pure aminoepoxide intermediates by chromatography is described, like Reetz and Binder, supra, Ng et al. recommend that the diastereoisomeric mixture of the aminoepoxide intermediate be used directly for further elaboration of the ultimate end product, saving the separation of diastereoisomers for a later stage.

The Ng et al. process has the disadvantages of (1) requiring chromatographic separation of the diasteroisomeric mixture to obtain the desired isomerically pure intermediate; (2) using pyrophoric butyllithium; and (3) forming an environmentally undesirable side product, namely butyliodide.

Similarly to the Ng et al. patent application, J. Barluenga et al., J. Chem. Soc., Chem. Commun., 1994, 969, disclose the preparation of a N,N-doubly protected aminoepoxide intermediate by reacting N,N-dibenzylalaninal with chloromethyllithium generated in situ from chloroiodomethane and methyllithium. This preparation has disadvantages similar to those as noted in the preceding paragraph.

The present process, on the other hand, fulfills the need for a safe, efficient process that can be worked on a large scale. The process has the features of simplicity and expediency, and it avoids the use of hazardous chemicals. The process efficiently and economically produces the desired intermediate, or a chemical equivalent thereof, with an enantiomeric and diastereomeric purity of 95% or greater.

SUMMARY OF THE INVENTION

Disclosed herein is a process for preparing a hydrochloric acid addition salt of an isomerically pure chlorohydrin of formula 1

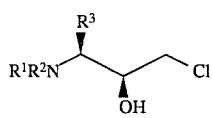

wherein $R^1$ and $R^2$ each independently is an N-benzyl protective group selected from benzyl or benzyl monosubstituted or disubstituted with (1–4C) alkyl, (1–4C)alkoxy or halo, and $R^3$ is an amino acid side chain or a protected amino acid side chain, which comprises the following steps:

(a) reacting an aldehyde of formula 2

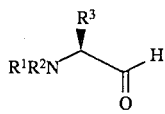

wherein $R^1$, $R^2$ and $R^3$ are as defined herein with (chloromethyl)lithium in an inert solvent at $-76°$ C. to $-20°$ C. to obtain a diastereoisomeric mixture of lithium alcoholates of formula 3 and formula 4, i.e.

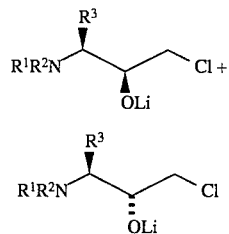

wherein $R^1$, $R^2$ and $R^3$ are as defined herein, the (chloromethyl)lithium being generated in situ in the reaction mixture by a metered series of tandem additions thereto of portions of bromochloromethane and of lithium metal so that the temperature of the reaction mixture is maintained at $-20°$ C. or below;

(b) while maintaining the temperature of the aforementioned reaction mixture at $-20°$ C. or below, separating unreacted lithium metal from the reaction mixture to obtain a chilled solution of the mixture of the lithium alcoholates in the inert solvent;

(c) transforming the mixture of the lithium alcoholates into a corresponding mixture of hydrochloric acid addition salts by immediately contacting the aforementioned chilled solution of the mixture of the lithium alcoholates with aqueous hydrochloric acid to obtain an inert solvent/aqueous hydrochloric acid solution of the hydrochloric acid addition salt of the chlorohydrin of formula 1 in admixture with a hydrochloric acid addition salt of a chlorohydrin of formula 5

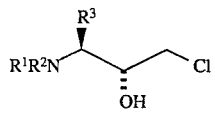

wherein $R^1$, $R^2$ and $R^3$ are as defined herein;

(d) removing the inert solvent from the inert solvent/ aqueous hydrochloric acid solution to obtain an aqueous phase and a water-insoluble phase, the latter phase comprising the mixture of the hydrochloric acid additions salts of the chlorohydrins;

(e) separating the water-insoluble phase from the aqueous phase;

(f) preparing a concentrated solution of the water-insoluble phase in a lower alkanol; and (g) selectively crystallizing the desired hydrochloric acid addition salt of the isomerically pure chlorohydrin of formula 1 from the lower alkanol solution.

Another aspect of the present invention involves the deprotection of the hydrochloric acid addition of the isomerically pure chlorohydrin of formula 1 by hydrogenolysis to give the hydrochloric acid addition salt of the isomerically pure compound of formula 6

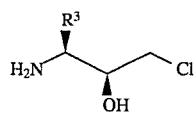

wherein $R^3$ is as defined herein.

DETAILS OF THE INVENTION

The term "isomerically pure" or isomeric purity" as used herein with reference to a compound means that the compound has an enantiomeric and diastereomeric purity of 95% or greater as determined by high performance liquid chromatography analysis using a column with a chiral support.

The term "amino acid" or "α-amino acid" as used herein means an α-amino acid having an (S)configuration at the α-carbon but excludes glycine. The term is not meant to be limiting other than it applies to α(S)-amino acids having a side chain containing at least one carbon atom attached to the α-carbon. The term therefore would encompass 19 of the 20 primary protein amino acids (i.e. those coded by DNA, except for glycine), other naturally occurring α-amino acids and synthetic α-amino acids. Examples of the amino acids encompassed by this term include phenylalanine, valine, leucine, isoleucine, α-aminocyclohexylpropionic acid, ornithine, serine, tyrosine, asparagine, cysteine, arginine and the like.

The term "amino acid side chain" as used herein means the radical of one or more carbon atoms attached to the α-carbon of an amino acid. It is the characterizing portion of an amino acid and is derived from a corresponding amino acid by elimination of the $NH_2CHC(O)OH$ moiety. For example, the amino acid side chain of phenylalanine is the phenylmethyl radical. The practicality of preparing the hydrochloric acid addition salt of the isomerically pure halohydrin of formula 1 having the latter amino acid side chain (i.e. $R^3$ is phenylmethyl) is demonstrated by example 1 hereinafter. Examples of other amino acid side chains ($R^3$) for the compounds of formulae 1 to 6 are 2-methylpropyl from leucine, 1-methylethyl from valine and methyl from alanine.

The term "protected amino acid side chain" as used herein means an amino acid side chain as described above which in addition bears a protected functional group. Protecting groups for functional groups are well known in the peptide art and are intended to protect such functional groups as amino, hydroxy, thio or carboxy against undesirable reactions during synthetic procedures. Examples of protected amino acid side chains ($R^3$) for the compounds of formula 1 to 6 would therefore include 3-(N,N-dibenzylamino)propyl derived from ornithine, benzyloxymethyl derived from serine, (4-methoxyphenyl)methyl derived from tyrosine, and {4-(phenylmethoxy)phenyl}methyl also derived form tyrosine.

The term "N-protecting group" or "N-protected" as used herein refers to groups intended to protect nitrogen atoms against undesirable reactions during chemical synthesis. Examples of N-protecting groups include tert-butyloxycarbonyl (Boc), benzyloxycarbonyl (Z) and benzyl (Bzl).

The term "(1–4C)alkyl" as used herein means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl and 1,1-dimethylethyl.

The term "(1–4C)alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy.

The term "halo" as used herein means a halo radical selected from bromo, chloro, fluoro or iodo.

The term "lower alkanol" as used herein means straight chain alkanols containing from one to four carbon atoms and branched chain alkanols containing three to four carbon atoms and includes methanol, ethanol, 1-methylethanol, 1,1-dimethylethanol, propanol, 2-methylpropanol and butanol.

The starting materials for the present process, i.e. the aldehydes of formula 2, are either known or can be prepared by standard methods. One general method for the preparation of the aldehydes has been described by M. T. Reetz et ,al., Angew. Chem. Int. Ed. Engl., 1987, 26, 1141. An example of an aldehyde of formula 2 described in the literature is α(S)-[bis(phenylmethyl)amino]benzenepropanal described by M. T. Reetz and M. W. Drewes, U.S. Pat. No. 4,990,669, issued Feb. 5, 1991, and J. S. Ng et al., PCT patent application WO 93/23388, published Nov. 25, 1993.

PROCESS

The key step of the process of this invention is the reaction of the aldehyde of formula 2 with (chloromethyl)lithium in an inert solvent at a temperature ranging from −76° C. to −20° C., preferably −76° C. to −60° C., to give the diastereoisomeric mixture of the lithium alcoholates of formulae 3 and 4. A relevant factor contributing to the efficacy of this step is the metrical or portionwise in situ generation of (chloromethyl)lithium from bromochloromethane and lithium in the solution of the aldehyde of formula 2 in the inert solvent. The reaction of bromochloromethane with lithium is exothermic and the product, (chloromethyl)lithium, is highly prone to thermal instability; for example, see K. M. Sadhu and D. S. Matteson, Tetrahedron Letters,1986, 27, 795. It has now been found that the disadvantages associated with the use of (chloromethyl)lithium can be overcome by generating the reagent in the reaction mixture in a semi-continuous manner. Accordingly, the (chloromethyl)lithium is generated in this instance by subjecting the stirred solution of the aldehyde of formula 2 to a series of tandem additions, each tandem addition consisting of (1) adding a portion of bromochloromethane and then a portion of lithium in a molar equivalent ratio ranging from 1:4 to 1:20, respectively. The series of tandem additions are done at a rate which allows the heat of reaction ensuing from the in situ generation of the (chloromethyl)lithium to be conducted away from the reaction mixture by conventional cooling means. In this manner, the temperature of the reaction can be maintained within a range of −76° C. to −20° C., preferably −76° C. to −60° C.

More particularly with respect to the key step of the process, a solution of the aldehyde of formula 2 in an inert solvent is cooled to between −76° C. and −20° C., preferably between −76° C. and −60° C., in a suitable reaction vessel. Suitable inert solvents include various ethers, for example, tetrahydrofuran, dioxane, 1,2-dimethoxyethane and diethyl ether.

Thereafter, (chloromethyl)lithium is generated in situ in the cooled solution in the following manner: Under an inert argon atmosphere, the vigorously stirred, cooled solution is subjected to a series of portionwise additions of first bromochloromethane and then lithium metal (shot or wire). (Note: the lithium wire or shot should be ground briefly, prior to their addition, to expose fresh metal surfaces.)

The series of additions are performed at a rate which allows for sufficient removal of the ensuing heat of reaction by external cooling of the reaction vessel. In this manner, the temperature of the reaction mixture is controlled and maintained at −20° C. or below. Depending on the size and scale of the reaction mixture, the reaction time for this key step usually is from 30 minutes to five hours.

In total, about 1.1 to 1.5 molar equivalents of bromochloromethane and about 5 to 20 molar equivalents of lithium are added to one molar equivalent of the aldehyde of formula 2.

The completion of the reaction can be monitored by various analytical techniques including thin layer chromatography.

At the completion of the reaction, i.e. the key step, the stirring is stopped, the reaction mixture is maintained at a temperature of −20° C. or below, preferably at −60° C. or below, and the unreacted lithium metal is allowed to float on the surface of the reaction mixture. The chilled liquid phase of the reaction mixture is immediately separated from the lithium metal and mixed with an aqueous solution of excess hydrochloric acid. In practice, the liquid phase can be conveniently separated by suction. A laboratory suction system capable of transferring the liquid phase away from the metal and into contact with the aqueous solution of excess hydrochloric acid is a convenient manner to accomplish this part of the process. Alternatively, the separation can be done by gravity or by suction filtration by opening a stop-cocked outlet system provided at the bottom of the reaction vessel.

The resulting inert solvent/aqueous hydrochloric acid solution is concentrated under reduced pressure (i.e. the inert solvent is removed from the latter solution by distillation under reduced pressure) to give a clear aqueous phase and a water insoluble oily residue. The aqueous phase is decanted from the oily residue. Next, a concentrated solution of the oily residue in a lower alkanol, preferably methanol or ethanol, is prepared. Upon standing the desired hydrochloric acid addition salt of the compound of formula 1 selectively crystallizes from the solution. Recrystallization of the hydrochloride salt from a lower alkanol, preferably methanol or ethanol, yields the desired chlorohydrin hydrochloride salt in about a 40% yield from the aldehyde of formula 2 with a 95% isomeric purity or greater as determined by high performance liquid chromatography analysis using a column with a chiral support.

Thereafter, if desired, the hydrochloric acid addition salt of the compound of formula 1 can be deprotected to give the hydrochloric acid addition salt of α-(chloromethyl)-β-aminoalcohol of formula 6 by subjecting the compound of formula 1 salt to hydrogenolysis methods capable of converting a benzyl-protected amino group to an amino group.

A convenient and practical method for effecting the deprotection involves subjecting the hydrochloric acid addition salt to hydrogenolysis using gaseous hydrogen or using a hydrogen transfer agent for example, ammonium formate, in the presence of a noble metal catalyst, such as platinum or palladium. The noble metal catalyst can be employed in the form of oxides (e.g. $PtO_2$) or hydroxides [e.g. $Pd(OH)_2$], on a suitable support (e.g. charcoal or calcium carbonate in a finely divided form).

If desired, the latter hydrochloric acid addition salt of the compound of formula 6 can be transformed to a corresponding N-(monoprotected)-aminoepoxide intermediate of formula A. The transformation can be effected by subjecting the hydrochloric acid addition salt of the compound of formula 6 to known methods for converting amino groups to N-(monoprotected)-amino groups to obtain the corresponding N-(monoprotected)-α-(chloromethyl)-β-aminoalcohol of formula 7

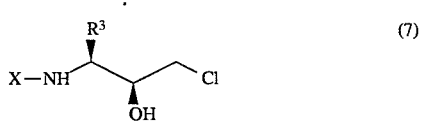

(7)

wherein X is a N-protective group and $R^3$ is as defined herein; followed by reacting the N-(monoprotected)-α-(chloromethyl)-β-aminoalcohol of formula 7 with a base (e.g. sodium hydroxide, potassium hydroxide or potassium carbonate) to give the corresponding N-(monoprotected)-aminoepoxide of formula A wherein X is a N-protective group, Y is hydrogen and R is a amino acid side chain or a protected amino acid side chain and the carbon atom bearing the nitrogen atom and the carbon atom bearing the oxygen atom both have the (S) configuration.

Finally, it will be appreciated by those familiar with the art that N-(monoprotected)-aminoepoxide of formula 1, and the hydrochloric acid addition salts of formula 1 and 6 are useful intermediates for the elaboration of HIV protease inhibitors. Also, it will likewise be appreciated that the process described herein can be used to prepare the corresponding enantiomers of the chlorohydrin of formulae 1 and 6 in the form of hydrochloric acid addition salts, i.e. the corresponding (R,R) enantiomers, by using the (R) enantiomer of the aldehyde of formula 2 as starting material.

The following examples further illustrate this invention. Solution percentages or ratios express a volume to volume relationship. Nuclear magnetic resonance (NMR) spectra were recorded on a Bruker AMX400 spectrometer and referenced to trimethylsilane as the internal standard; the chemical shifts (δ) are reported in parts per million. Optical rotations were recorded on a Perkin Elmer 241 MC polarimeter at the D line of sodium with a 1 dm path length, 1 mL cell; the concentrations are expressed in grams of compound per 100 mL of solution. High performance liquid chromatography (HPLC) analyses were performed using a C18 reversed phase column, aqueous trifluoroacetic acid and acetonitrile gradients and UV detection (230 nm). Abbreviations and symbols used in the examples include Boc: tert-butyloxycarbonyl; $Et_2O$: diethyl ether; MeOH: methanol and THF: tetrahydrofuran.

EXAMPLE 1

Preparation of β(S)-[bis(phenylmethyl)amino]-α(S)-(chloromethyl)benzenepropanol hydrochloric acid addition salt (the hydrochloric acid addition salt of the chlorohydrin of formula 1 wherein $R^1$, $R^2$ and $R^3$ are phenylmethyl).

A solution of α(S)-[bis(phenylmethyl)amino]-benzenepropanal (2233 g, 6.77 mol) in reagent grade THF (22.3 L) was placed in a 50 L three-necked flask equipped with a mechanical stirrer and a low temperature thermometer. The solution was cooled to an internal temperature of −76° C. Under an argon atmosphere, the mixture was stirred vigorously. Bromochloromethane (245 g, 123 mL, 1.893 mol) was added in one portion to the stirred solution followed by the addition of lithium shot (Aldrich Chemical Co., Milwaukee, Wis., U.S.A., catalog #22,849-4, 180 g, 25.9 mol). (The lithium shot was ground briefly in a mortar, just prior to their addition, to expose fresh metal surfaces.) The internal temperature rose to −67° C. over the next 30 min. After an additional 15 min, the temperature started to drop. A second portion of the reagents, i.e. bromochloromethane (245 g) and lithium shot (180 g), was added. After an initial temperature rise to −64° C., the reaction mixture was allowed to cool down to −72° C. before a third portion of the reagents was added at time 120 min from the start of the reaction. The last portion of the reagents was added at time 2.5 h and the reaction mixture was stirred for one hour more. In all, bromochloromethane (980 g, 7.57 mol) and lithium shot (720 g, 104 mol) were added in four equal portions while carefully keeping the internal temperature of the reaction mixture below −60° C. at all times. The total reaction time was 3.5 h from the first addition.

After completion of the reaction, the stirring was stopped and the unreacted lithium metal was allowed to float to the surface of the reaction mixture. The liquid phase (still at −72° C.) was suctioned from the bottom of the reaction vessel into 7 L of aqueous 6N HCl. The lithium shot remaining in the flask was washed with THF (1 L) and the washings were added to the hydrochloric acid solution. (The lithium shot was recovered by suction filtration, washed with THF and hexane, and dried under reduced pressure for future use.)

The THF/aqueous hydrochloric acid solution was concentrated under reduced pressure until a clear aqueous phase separated from a brown gummy residue. The aqueous layer was removed by decantation. The residue was washed with $H_2O$ (3×1 L) and then dissolved in 3 L of warm MeOH. The solution was allowed to stand at 5° C. for 18h. The resulting precipitate was collected by suction filtration and washed with 10% MeOH in $Et_2O$ (2×500 mL). (The filtrate was discarded because it contained very little material, but the washes were set aside for recovery of a second crop.) The precipitate was dried under reduced pressure to give the crude title compound as a tan-colored solid (1128 g, 77% pure by HPLC). Concentration of the aforementioned washes gave a second crop (105 g, 73% pure by HPLC).

The two crops (1233 g total) were combined and dissolved in warm MeOH (4 L). After cooling overnight at 5° C., the crystalline material from the solution was collected on a filter, washed with 10% MeOH in $Et_2O$ (500 mL) and dried under reduced pressure to give the pure title compound (750 g, 94% pure by HPLC). The preceding mother liquor and washes were combined. The resulting solution was concentrated to 800 mL and cooled overnight at 5° C. to give a second crop (262 g, 90% pure by HPLC). From the latest mother liquor and washings, a third crop was obtained (52 g, 81% pure by HPLC). The total yield of recrystallized material (3 crops) was 1064 g (38% overall yield from α(S)-[bis(phenylmethyl)amino]propanal) with a HPLC purity of 89%, $[\alpha]_D^{23}$ −7.3° (c=1, MeOH), mp 172°–174° C. (dec.). The $^1$H NMR (400 MHz, $CD_3OD$) of the title compounds showed δ 2.69 (t, J=10.3 Hz, 1H), 3.05 (dd, J=11.0 Hz, 1H), 3.31 (m, 1H), 3.39 (dd, J=13.7, 4.0 Hz, 1H), 3.53 (dd, J=14.0, 9.9 Hz, 1H), 3.99 (broad d, J=6.3 Hz, 1H), 4.5 (m, 3H), 4.72 (broad d, J =14.0 Hz, 1H), 5.03 (broad d, J=13.2 Hz, 1H), 7.13 (m, 2H), 7.28 (m, 3H) , 7.5 (m, 10H); FAB mass spectrum, m/z: 380 (M+H)$^+$.

The isomeric purity of the title compound in its free base form was determined by normal phase HPLC on a Chiracel® OD column from Daicel Chemical Industries Limited, Tokyo, Japan (U.S. distributor: Chiral Technologies Inc., Exton Pa., U.S.A.). EtOH-hexane (1:19) was the eluent and UV detection at 205 run was employed. The sample of the hydrochloric acid addition salt was neutralized with NaHCO$_3$ or Na$_2$CO$_3$, and extracted into hexane prior to analysis. The isomeric purity of the title compound was >99.5%.

By following the procedure of example 1 but replacing α(S)-[bis(phenylmethyl)amino]benzene-propanal with an equivalent amount of 2(S)-[bis(phenylmethyl)amino]-4-methylpentanal, the hydrochloric acid addition salt of 2(S)-[bis(phenylmethyl)amino]-1(S)-(chloromethyl)-4-methylpentanol (1: R$^1$ and R$^2$ are phenylmethyl and R$^3$ is 2-methylpropyl) was obtained; $[\alpha]_D^{23}$ 32 +1.5° (c =1, MeOH); mp 165°–166° C.; FAB mass spectrum, m/z: 346 (M+H)$^+$. The isomeric purity of the latter compound was >98%.

Again, by following the procedure of example 1 but replacing α(S)-[bis(phenylmethyl)amino]benzenepropanal with an equivalent amount of 2(S)-[bis(phenylmethyl)amino]-3-methylbutanal, the hydrochloric acid addition salt of 2(S)-[bis (phenylmethyl)amino]-1(S)-(chloromethyl)-3-methylbutanol (1; R$^1$ and R$^2$ are phenylmethyl and R$^3$ is 1-methylethyl) was obtained; $[\alpha]_D^{23}$=−52.8° (c=1, MeOH); mp 164°–165° C.; FAB mass spectrum, m/z: 332 (M+H)$^+$. The isomeric purity of the latter compound was >99%.

Again, by following the procedure of example 1 but replacing α(S)-[bis(phenylmethyl)amino]-benzenepropanal with an equivalent amount of 2(S)-[bis(phenylmethyl)amino]propanal, the hydrochloric acid addition salt of 2(S)-[bis(phenylmethyl)amino]-1(S)-(chloromethyl)propanol (1; R$^1$ and R$^2$ are phenylmethyl and R$^3$ is methyl) was obtained; $[\alpha]_D^{23}$=−21.3° (c=1, MeOH); mp 170°–173° C.; FAB mass spectrum, m/z: 304 (M+H)$^+$. The isomeric purity of the latter compound was >98%.

Again, by following the procedure of example 1 but replacing α(S)-[bis(phenylmethyl)amino]benzenepropanal with an equivalent amount of α(S)-[bis(phenylmethyl)amino]-4-(phenylmethoxy)phenyl-propanal, the hydrochloric acid addition salt of β(S)-[bis(phenylmethyl)amino]-α(S)-(chloromethyl)-4-(phenylmethoxy) phenylpropanol {(1; R$^1$ and R$^2$ are phenylmethyl and R$^3$ is {4-(phenylmethoxy)phenyl)-methyl was obtained; $[\alpha]_D^{23}$=+12.7° (c=1, MeOH); mp 178°–180° C.; FAB mass spectrum, m/z: 486 (M+H)$^+$. The isomeric purity of the latter compounds was >97%.

EXAMPLE 2

Preparation of β(S)-amino-α(S)-(chloromethyl)-benzenepropanol hydrochloric acid addition salt (the hydrochloric acid addition salt of the compound of formula 6 wherein R$^3$ is phenylmethyl).

The title compound of example 1 (53.6 g, 0.129 mol) and the catalyst 20% Pd(OH)$_2$ on charcoal (5.0 q) were suspended in MeOH (500 mL) in a 1 L three-necked flask. The suspension was stirred at 20°–22° C. under an atmosphere of hydrogen for 18 h. Thereafter, the catalyst was removed by filtration through a glass filter. The collected catalyst was washed with MeOH. The combined filtrate and washings were concentrated to dryness under reduced pressure. The solid residue was triturated with Et$_2$O, collected on a filter and dried under reduced pressure to give the title compound. (29.6 g, 97% yield, 97% purity by HPLC) as a white solid; $[\alpha]_D^{23}$ −42.5° (c=1, MeOH), mp 204°–208° C.

EXAMPLE 3

(The following is an example of an N-(monoprotected)-aminoepoxide intermediate of formula A.)

Preparation of 3(S)-(tert-butyloxycarbonylamino)1,2(S)-epoxy-4-phenylbutane (the compound of formula A wherein X is Boc, Y is hydrogen and R is phenylmethyl, and the carbon atom bearing the nitrogen and the carbon atom bearing the oxygen atom both have the (S) configuration).

A solution of di-tert-butyl dicarbonate (1320 g, 6.046 mol) and triethylamine (1.7 L, 12.18 mol) in reagent grade THF (10 L) was cooled to 1° C. Under an atmosphere of nitrogen, the title compound of example 2 (1418 g, 6.00 mol) was added in portions (as a solid) to the stirred solution over a 30 min period, keeping the temperature of the reaction mixture below 15° C. Thereafter, the reaction mixture was stirred at ambient temperature (20°–22° C.) for 3h.

The reaction mixture was cooled to an internal temperature of 5°–7° C. A solution of KOH (1344 g, 24 mol) in MeOH (5.3 L) was added over a 15 min period, keeping the temperature of the reaction mixture below 15°C. Thereafter, the reaction mixture was stirred at ambient temperature for 75 min. (Thin layer chromatography (SiO$_2$, hexane/ethyl acetate, 4:1) indicated that the reaction was complete).

The reaction mixture was poured into H$_2$O (60 L). The precipitate was collected on a filter by suction, washed to neutral pH with H$_2$O (60 L) and air-dried by suction on the filter to give the title compound as fine white needles (1530 g, 96% yield, 90% pure by HPLC). The material was sufficiently pure for further use. Recrystallization of a sample from MeOH gave the pure title compound of this example $[\alpha]_D^{23}$+6.9° (c=1, chloroform); mp 124°–125° C. The $^1$H NMR (400, CDCl13) of the title compound showed δ 1.38 (s, 9H), 2.7–3.0 (m, 5H), 3.7 (broad m, 1H), 4.53 (d, J=8.3 Hz, 1H), 7.2–7.3 (m, 3H), 7.3–7.4 (m, 2H).

The embodiments of this invention in which an exclusive property or privilege is claimed are defined as follows:

1. A process for preparing a hydrochloric acid addition salt of an isomerically pure chlorohydrin of formula 1

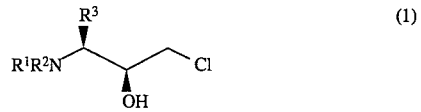

(1)

wherein R$^1$ and R$^2$ each independently is an N-benzyl protective group selected from benzyl or benzyl monosubstituted or disubstituted with (1–4C) alkyl, (1–4C)alkoxy or halo, and R$^3$ is an amino acid side chain or a protected amino acid side chain, which comprises the following steps:

(a) reacting an aldehyde of formula 2

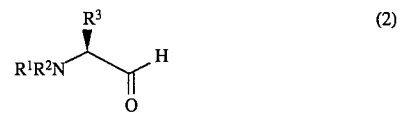

(2)

wherein R$^1$, R$^2$ and R$^3$ are as defined in this claim with (chloromethyl)lithium in an inert solvent at −76° C. to −20° C. to obtain a diastereoisomeric mixture of lithium alcoholates of formula 3 and formula 4

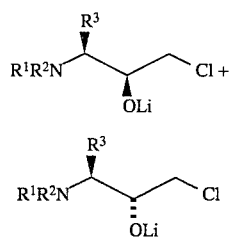

wherein $R^1$, $R^2$ and $R^3$ are as defined in this claim, the (chloromethyl)lithium being generated in situ in the reaction mixture by a metered series of tandem additions thereto of portions of bromochloromethane and of lithium metal so that the temperature of the reaction mixture is maintained at $-20°$ C. or below;

(b) while maintaining the temperature of the aforementioned reaction mixture at $-20°$ C. or below, separating unreacted lithium metal from the reaction mixture to obtain a chilled solution of the mixture of the lithium alcoholates in the inert solvent;

(c) transforming the mixture of the lithium alcoholates into a corresponding mixture of hydrochloric acid addition salts by immediately contacting the aforementioned chilled solution of the mixture of the lithium alcoholates with aqueous hydrochloric acid to obtain an inert solvent/aqueous hydrochloric acid solution of the hydrochloric acid addition salt of the chlorohydrin of formula 1 in admixture with a hydrochloric acid addition salt of a chlorohydrin of formula 5

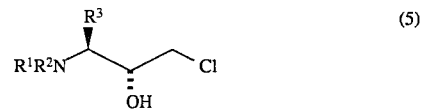

wherein $R^1$, $R^2$ and $R^3$ are as defined in this claim;

(d) removing the inert solvent from the inert solvent/aqueous hydrochloric acid solution to obtain an aqueous phase and a water-insoluble phase, the latter phase comprising the mixture of the hydrochloric acid additions salts of the chlorohydrins;

(e) separating the water-insoluble phase from the aqueous phase;

(f) preparing a concentrated solution of the water-insoluble phase in a lower alkanol; and (g) selectively crystallizing the desired hydrochloric acid addition salt of the isomerically pure chlorohydrin of formula 1 from the lower alkanol solution.

2. The process of claim 1 wherein the lithium metal in step (a) is ground briefly to expose fresh metal surfaces prior to its addition to the reaction mixture.

3. The process of claims 1 or 2 wherein 1.1 to 1.5 molar equivalent of bromochloromethane and 5 to 20 molar equivalents of lithium metal, with respect to the aldehyde of formula 2, are added in step (a) to the reaction mixture.

4. The process of claims 1 or 2 wherein the temperature of the reaction mixture of steps (a) and (b) is maintained within the range of $-76°$ C. to $-60°$ C.

5. The process of claims 1 or 2 wherein $R^1$ and $R^2$ each is phenylmethyl and $R^3$ is selected from the group consisting of phenylmethyl, 2-methylpropyl, 1-methylethyl, methyl and {4-(phenylmethoxy)phenyl}methyl.

6. The process of claim 1 wherein step (a) is conducted under an atmosphere of argon and the inert solvent is selected from the group consisting of tetrahydrofuran, dioxane, 1,2-dimethoxyethane and diethyl ether.

7. The process of claim 1 including the additional step of deprotecting the hydrochloric acid addition salt of the isomerically pure chlorohydrin of formula 1 by hydrogenolysis to obtain the hydrochloric acid addition salt of an isomerically pure compound of formula 6

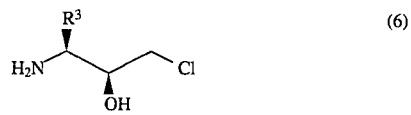

wherein $R^3$ is as defined in claim 1.

8. The process of claim 7 wherein $R^1$, $R^2$ and $R^3$ are benzylmethyl.

9. The process of claim 7 including the additional steps of transforming the hydrochloric acid addition salt of the isomerically pure compound of formula 6 wherein $R^3$ is as defined in claim 7 to a corresponding N-(monoprotected)-α-(chloromethyl)-β-aminoalcohol of formula 7

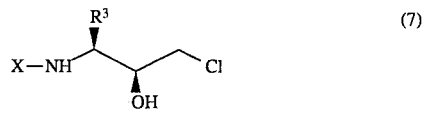

wherein X is a N-protective group and $X^3$ is as defined in claim 7; followed by reacting the N-(monoprotected)-α-(chloromethyl)-β-aminoalcohol of formula 7 with a base to obtain the corresponding N-(monoprotected)-aminoepoxide of formula A

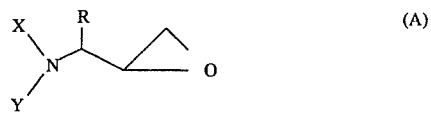

wherein X is a N-protective group, Y is hydrogen and R is a amino acid side chain or a protected amino acid side chain and the carbon atom bearing the nitrogen atom and the carbon atom bearing the oxygen atom both have the (S) configuration.

10. The process of claim 9 wherein $R^3$ and R are phenylmethyl, X is tert-butyloxycarbonyl and Y is hydrogen.

* * * * *